(12) United States Patent
Bellus et al.

(10) Patent No.: US 6,670,507 B2
(45) Date of Patent: Dec. 30, 2003

(54) PROCESS FOR THE PREPARATION OF ARYLOCTANOYL AMIDES

(75) Inventors: Daniel Bellus, Riehen (CH); Alessandro Dondoni, Ferrara (IT)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 10/342,254

(22) Filed: Jan. 15, 2003

(65) Prior Publication Data

US 2003/0176717 A1 Sep. 18, 2003

Related U.S. Application Data

(63) Continuation of application No. 10/014,400, filed on Dec. 14, 2001, now abandoned.

(30) Foreign Application Priority Data

Dec. 14, 2000 (CH) ................................................. 2442/00

(51) Int. Cl.$^7$ ..................... C07C 231/02; C07C 231/10; C07C 231/16; C07C 263/02; C07C 307/12
(52) U.S. Cl. ................ 564/134; 564/165; 548/216; 549/321; 556/410
(58) Field of Search ................................. 564/134, 165; 548/216; 549/321; 556/410

(56) References Cited

FOREIGN PATENT DOCUMENTS

EP          0 678 503          10/1995

OTHER PUBLICATIONS

A. Dondoni et al., "A Convergent Synthesis of the Renin Inhibitor SPP–100 Using a Nitrone Intermediate", Tetrahedron Lett., vol. 42, 2001, pp. 4819–4823.
D.A. Sandham et al., "A Convergent Synthesis of the Renin Inhibitor CGP60536B", Tetrahedron Lett., vol. 41, 2000, pp. 10091–10094.
D.D. Dhavale et al., "A New Route to Aminosugars From Sugar Nitrones: Synthesis of 6–Deoxynojirimycin", Tetrahedron: Asymmetry, vol. 8, No. 9, 1997, pp. 1475–1486.
Database CAPLUS on STN, Acc. No. 1995:995373, Goeschke, EP 678503, Oct. 25, 1995 (abstract).
Database CAPLUS on STN, Acc. No. 1994:655365, Hanessian, Biorg. Med. Chem. Lett. (1994), 4(14), p. 1697–702.
Rueger, H., et al. "A convergent synthesis approach towards CGP60536B, a non–peptide orally potent renin inhibitor, via an enantiomerically pure ketolactone intermediate", Tetrahedron Letters, vol. 41 (2000), pp. 10085–10089.

Primary Examiner—Brian Davis
(74) Attorney, Agent, or Firm—Wenderoth, Lind & Ponack, L.L.P.

(57) ABSTRACT

Compounds of formula I

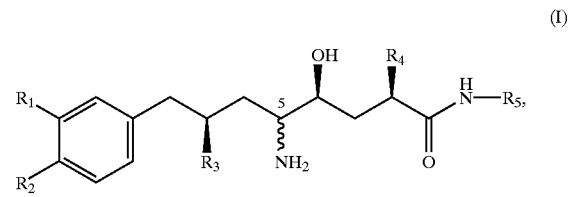

wherein $R_1$ is for example 3-methoxyprop-3-yloxy, $R_2$ is for example methoxy, $R_3$ and $R_4$ are in each case for example isopropyl, and $R_5$ is $H_2NC(O)$—$[C(CH_3)_2]$—$CH_2$—, are obtainable by reaction of compounds of formula IV

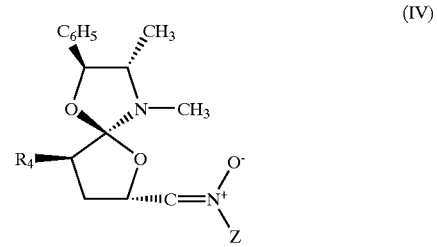

with a metal organic derivative of 1-(3-$R_1$-4-$R_2$-phen-1-yl)-2-$R_3$-3-halogen propanes to form a compound of formula VI,

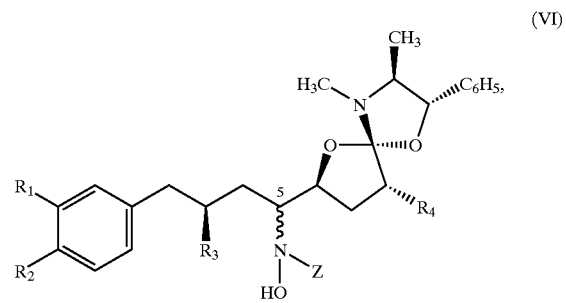

followed by removal of the pseudoephedrine protecting group and the OH group, reaction of the resulting lactone with an amine $R_5$—$NH_2$ and removal of protecting group Z.

23 Claims, No Drawings

PROCESS FOR THE PREPARATION OF ARYLOCTANOYL AMIDES

This application is a continuation of Ser. No. 10/014,400 filed Dec. 14, 2001 now abandoned.

The invention relates to a stereospecific method for the preparation of 2(S),4(S),7(S)-2,7-dialkyl-4-hydroxy-5-amino-8-aryloctanoyl amides in the form of 5(R)- or 5(S)-diastereomers and mixtures thereof, as well as their physiologically acceptable salts; and new compounds used in the multistage process as intermediates.

In EP-A-0 678 503, δ-amino-γ-hydroxy-ω-arylalkanecarboxamides are described, which exhibit renin-inhibiting properties and could be used as antihypertensive agents in pharmaceutical preparations. The manufacturing procedures described are unsatisfactory in terms of the number of process steps and yields and are not suitable for an industrial process. A disadvantage of these processes is also that the total yields of pure diastereomers that are obtainable are too small.

D. A. Sandham et al. describe in Tetrahedron Letters, Volume 41, Issue 51, pages 10085–10089 (2000), a synthesis for the preparation of 2(S),4(S),5(S),7(S)-2-isopropyl-4-hydroxy-5-amino-7-isopropyl-8-[(3-methoxy-n-propoxy)-4-methoxyphenyl]octanoyl amide, in which a Grignard compound of 1-[(3-methoxy-n-propoxy)-4-methoxyphenyl]-2-isopropyl-3-chloropropane is reacted with a pseudoephedrine-protected isopropylvalerolactone aldehyde, followed by hydrolysis, to form a compound of formula A

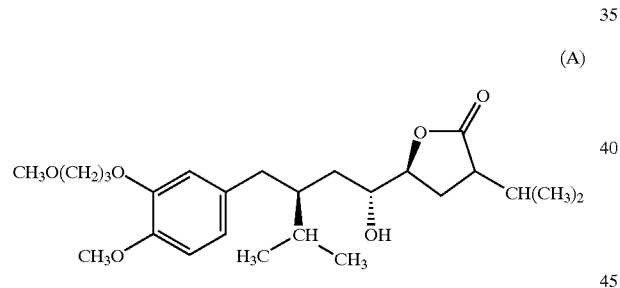

(A)

The compound of formula A is obtained in a yield of only 51%, the R:S ratio, in relation to the OH group, being 85:15. The OH group is then converted to a leaving group (brosylate). The reaction with sodium azide yields the corresponding azido compound which with 3-amino-2,2-dimethylpropionamide on opening of the lactone ring gives the corresponding amide. Catalytic hydrogenation then yields the desired amine.

It has now been surprisingly found that these alkanecarboxamides are obtainable both in high total yields and in a high degree of purity when the amino group is introduced with Grignard coupling. According to this process step, customary purification and separation procedures can if necessary be used for the preparation of pure diastereomers. The process is suitable for industrial scale manufacture.

A first object of the invention is a process for the preparation of compounds of formula I and their physiologically acceptable salts,

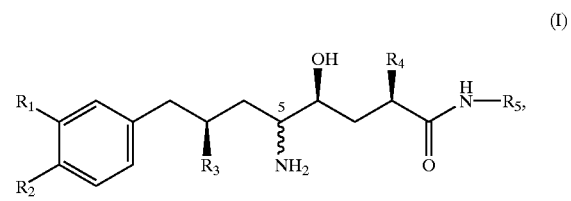

(I)

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$-alkyl, $C_1$–$C_6$alkanoyloxy-$C_1$–$C_6$alkyl, $C_1$–$C_6$aminoalkyl, $C_1$–$C_6$alkylamino-$C_1$–$C_6$-alkyl, $C_1$–$C_6$-dialkylamino-$C_1$–$C_6$-alkyl, $C_1$–$C_6$-alkanoylamido-$C_1$–$C_6$-alkyl, HO(O)C—$C_1$–$C_6$-alkyl, $C_1$–$C_6$alkyl-O—(O)C—$C_1$–$C_6$alkyl, $H_2$N—C(O)—$C_1$–$C_6$alkyl, $C_1$–$C_6$alkyl-HN—C(O)—$C_1$–$C_6$alkyl or ($C_1$–$C_6$alkyl)$_2$N—C(O)—$C_1$–$C_6$-alkyl, comprising the steps a) reaction of a compound of formula II,

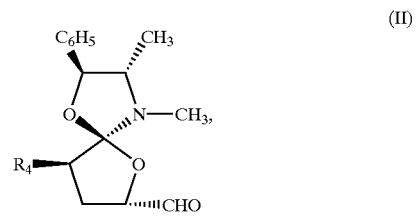

(II)

wherein $R_4$ is as defined above, with a hydroxylamine of formula ZNHOH (III), wherein Z is a removable protecting group, to form a compound of formula IV,

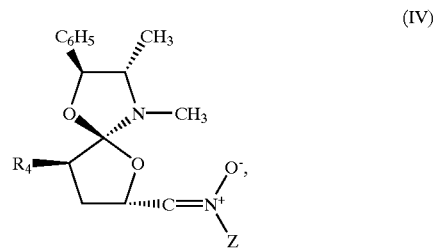

(IV)

b) reaction of a compound of formula IV with a metal organic derivative of a compound of formula V,

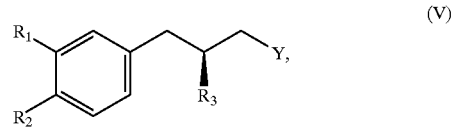

(V)

wherein $R_1$, $R_2$ and $R_3$ are as defined above, and Y is Cl, Br or I, to form a compound of formula VI,

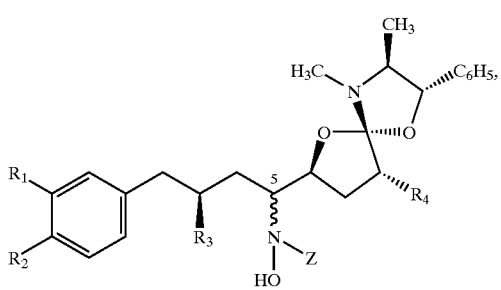

(VI)

c) removal of the hydroxyl group to form a compound of formula VII,

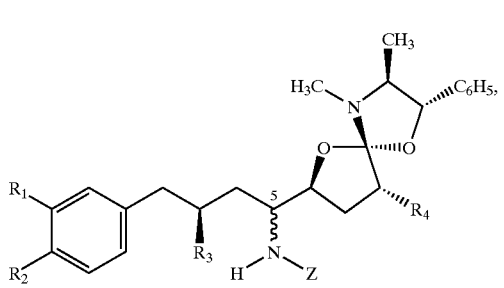

(VII)

d) removal of the pseudoephedrine protecting group to form compounds of formula VIII,

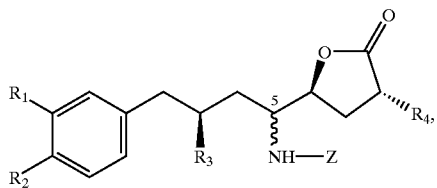

(VIII)

or the performance of step d) before step c), or the performance of steps c) and d) together in one reaction vessel, e) reaction of a compound of formula VIII with an amine of formula $R_5$—$NH_2$ to form a compound of formula IX

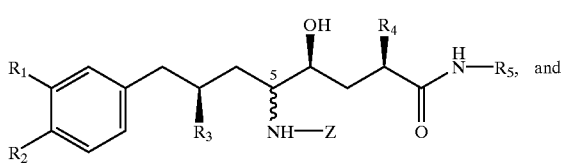

(IX)

f) removal of protecting group Z for the preparation of compounds of formula I.

With the process according to the invention, preferably the 5(S)-diastereomer of formula Ia

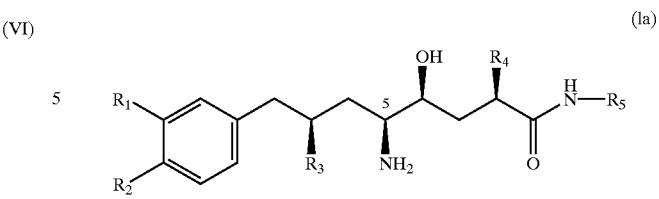

(Ia)

As an alkyl, $R_1$ and $R_2$ may be linear or branched and preferably comprise 1 to 4 C atoms. Examples are methyl, ethyl, n- and i-propyl, n-, i- and t-butyl, pentyl and hexyl.

As a halogenalkyl, $R_1$ and $R_2$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ and $R_2$ may be linear or branched. The alkoxy group preferably comprises 1 to 4 and especially 1 or 2 C atoms, and the alkyl group preferably comprises 1 to 4 C atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

As a $C_1$–$C_6$alkoxy-$C_1$–$C_6$alkyloxy, $R_1$ and $R_2$ may be linear or branched. The alkoxy group preferably comprises 1 to 4 and especially 1 or 2 C atoms, and the alkyloxy group preferably comprises 1 to 4 C atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy- or ethoxy-$C_1$–$C_4$alkyloxy, and $R_2$ is preferably methoxy or ethoxy. Particularly preferred are compounds of formula I, wherein $R_1$ is 1-methoxyprop-3-yloxy and $R_2$ is methoxy.

As an alkyl, $R_3$ and $R_4$ may be linear or branched and preferably comprise 1 to 4 C atoms. Examples are methyl, ethyl, n- and i-propyl, n-, i- and t-butyl, pentyl and hexyl. In a preferred embodiment, $R_3$ and $R_4$ in compounds of formula I are in each case isopropyl.

As an alkyl, $R_5$ may be linear or branched and preferably comprise 1 to 4 C atoms. Examples of alkyl are listed hereinabove. Methyl, ethyl, n- and i-propyl, n-, i- and t-butyl are preferred.

As a $C_1$–$C_6$hydroxyalkyl, $R_5$ may be linear or branched and preferably comprise 2 to 6 C atoms. Some examples are 2-hydroxyethy-1-yl, 2-hydroxyprop-1-yl, 3-hydroxyprop-1-yl, 2-, 3- or 4-hydroxybut-1-yl, hydroxypentyl and hydroxyhexyl.

As a $C_1$–$C_6$alkoxy-$C_1$–$C_6$alkyl, $R_5$ may be linear or branched. The alkoxy group preferably comprises 1 to 4 C atoms and the alkyl group preferably 2 to 4 C atoms. Some examples are 2-methoxyethy-1-yl, 2-methoxyprop-1-yl, 3-methoxyprop-1-yl, 2-, 3- or 4-methoxybut-1-yl, 2-ethoxyethy-1-yl, 2-ethoxyprop-1-yl, 3-ethoxyprop-1-yl, and 2-, 3- or 4-ethoxybut-1-yl.

As a $C_1$–$C_6$alkanoyloxy-$C_1$–$C_6$alkyl, $R_5$ may be linear or branched. The alkanoyl group preferably comprises 1 to 4 C atoms and the alkyl group preferably 2 to 4 C atoms. Some examples are formyloxymethyl, formyloxyethyl, acetyloxyethyl, propionyloxyethyl and butyroyloxyethyl.

As a $C_1$–$C_6$aminoalkyl, $R_5$ may be linear or branched and preferably comprise 2 to 4 C atoms. Some examples are 2-aminoethyl, 2- or 3-aminoprop-1-yl and 2-, 3- or 4-aminobut-1-yl.

As a $C_1$–$C_6$alkylamino-$C_1$–$C_6$alkyl and $C_1$–$C_6$dialkylamino-$C_1$–$C_6$-alkyl, $R_5$ may be linear or branched. The alkylamino group preferably comprises $C_1$–$C_4$alkyl groups and the alkyl group preferably 2 to 4 C atoms. Some examples are 2-methylaminoeth-1-yl, 2-dimethylaminoeth-1-yl, 2-ethylaminoeth-1-yl, 2-ethylaminoeth-1-yl, 3-methylaminoprop-1-yl, 3-dimethylaminoprop-1-yl, 4-methylaminobut-1-yl and 4-dimethylaminobut-1-yl.

As a $C_1$–$C_6$alkanoylamido-$C_1$–$C_6$alkyl, $R_5$ may be linear or branched. The alkanoyl group preferably comprises 1 to 4 C atoms and the alkyl group preferably 1 to 4 C atoms. Some examples are 2-formamidoeth-1-yl, 2-acetamidoeth-1-yl, 3-propionylamidoeth-1-yl and 4-butyroylamidoeth-1-yl.

As a HO(O)C—$C_1$–$C_6$alkyl, $R_5$ may be linear or branched, and the alkyl group preferably comprises 2 to 4 C atoms. Some examples are carboxymethyl, carboxyethyl, carboxypropyl and carboxybutyl.

As a $C_1$–$C_6$-alkyl—O—(O)C—$C_1$–$C_6$alkyl, $R_5$ may be linear or branched, and the alkyl groups preferably comprise independently of one another 1 to 4 C atoms. Some examples are methoxycarbonylmethyl, 2-methoxycarbonyleth-1-yl, 3-methoxycarbonylprop-1-yl, 4-methoxycarbonylbut-1-yl, ethoxycarbonylmethyl, 2-ethoxycarbonyleth-1-yl, 3-ethoxycarbonylprop-1-yl, and 4-ethoxycarbonylbut-1-yl.

As a $H_2N$—C(O)—$C_1$–$C_6$alkyl, $R_5$ may be linear or branched, and the alkyl group preferably comprises 2 to 6 C atoms. Some examples are carbamidomethyl, 2-carbamidoeth-1-yl, 2-carbamido-2,2-dimethyleth-1-yl, 2- or 3-carbamidoprop-1-yl, 2-, 3- or 4-carbamidobut-1-yl, 3-carbamido-2-methylprop-1-yl, 3-carbamido-1,2-dimethylprop-1-yl, 3-carbamido-3-methylprop-1-yl, 3-carbamido-2,2-dimethylprop-1-yl, 2-, 3-, 4- or 5-carbamidopent-1-yl, 4-carbamido-3,3- or -2,2-dimethylbut-1-yl.

As a $C_1$–$C_6$alkyl-HN—C(O)—$C_1$–$C_6$-alkyl or ($C_1$–$C_6$alkyl)$_2$N—C(O)—$C_1$–$C_6$-alkyl, $R_5$ may be linear or branched, and the NH-alkyl group preferably comprises 1 to 4 C atoms and the alkyl group preferably 2 to 6 C atoms. Examples are the carbamidoalkyl groups defined hereinabove, whose N atom is substituted with one or two methyl, ethyl, propyl or butyl.

A preferred subgroup of compounds of formula I is that in which $R_1$ is $C_1$–$C_4$alkoxy or $C_1$–$C_4$alkoxy-$C_1$–$C_4$alkyloxy, $R_2$ is $C_1$–$C_4$alkoxy, $R_3$ is $C_1$–$C_4$alkyl, $R_4$ is $C_1$–$C_4$alkyl and $R_5$ is $H_2NC(O)$—$C_1$–$C_6$alkyl which if necessary is N-monosubstituted or N-di-$C_1$–$C_4$alkyl substituted.

A more preferred subgroup of compounds of formula I is that in which $R_1$ is methoxy-$C_2$–$C_4$-alkyloxy, $R_2$ is methoxy or ethoxy, $R_3$ is $C_2$–$C_4$alkyl, $R_4$ is $C_2$–$C_4$alkyl and $R_5$ is $H_2NC(O)$—$C_1$–$C_6$alkyl.

An especially preferred compound of formula I is that in which $R_1$ is 3-methoxy-prop-3-yloxy, $R_2$ is methoxy, $R_3$ and $R_4$ are 1-methyleth-1-yl, and $R_5$ is $H_2NC(O)$—[C(CH$_3$)$_2$]—CH$_2$—.

Protecting groups Z in compounds of formula III are generally known. Preferred groups are those which can be removed by hydrogenation, such as silyl groups and preferably mono-, di- or triarylmethyl, special preference being for mono-, di- or triphenylmethyl. The aryl groups may be unsubstituted or substituted for example with halogen, $C_1$–$C_4$alkyl, $C_1$–$C_4$alkoxy or $C_1$–$C_4$halogenalkyl. Some examples are naphthylmethyl, methyl- or dimethylbenzyl, methoxy- or dimethoxybenzyl, chlorobenzyl, trifluoromethylbenzyl, benzyl, diphenylmethyl, di(methylphenyl)methyl, di(methoxyphenyl)methyl, trityl, tri(methylphenyl)methyl, tri(methoxyphenyl)methyl, trimethylsilyl, triphenylsilyl and methyldiphenylsilyl. Benzyl is especially preferred.

The individual process steps may be carried out in the presence of solvent. Suitable solvents are water and organic solvents, especially polar organic solvents, which can also be used as mixtures of at least two solvents. Examples of solvents are hydrocarbons (petroleum ether, pentane, hexane, cyclohexane, methylcyclohexane, benzene, toluene, xylene), halogenated hydrocarbon (methylene chloride, chloroform, tetrachloroethane, chlorobenzene); ether (diethyl ether, dibutyl ether, tetrahydrofuran, dioxane, ethylene glycol dimethyl or diethyl ether); carbonic ester and lactone (methyl acetate, ethyl acetate, methyl propionate, valerolactone); N,N-substituted carboxamides and lactams (dimethylformamide, dimethylacetamide, N-methylpyrrolidone); ketones (acetone, methylisobutylketone, cyclohexanone); sulfoxides and sulfones (dimethylsulfoxide, dimethylsulfone, tetramethylene sulfone); alcohols (methanol, ethanol, n- or i-propanol, n-, i- or t-butanol, pentanol, hexanol, cyclohexanol, cyclohexanediol, hydroxymethyl or dihydroxymethyl cyclohexane, benzyl alcohol, ethylene glycol, diethylene glycol, propanediol, butanediol, ethylene glycol monomethyl or monoethyl ether, and diethylene glycol monomethyl or monoethyl ether; nitriles (acetonitrile, propionitrile); tertiary amines (trimethyl-, triethyl-, tripropyl- and tributylamine, pyridine, N-methylpyrrolidine, N-methylpiperazine, N-methylmorpholine) and organic acids (acetic acid, formic acid).

Process Step a)

Compounds of formula II are known, and their preparation is described by D. A. Sandham et al. in Tetrahedron Letters, Volume 41, Issue 51, pages 10090ff (2000). The compounds of formula II are unstable. It is therefore recommended that the aldehyde be prepared immediately before the reaction with a hydroxylamine. To this end, the corresponding alcohol is oxidized to the aldehyde for example with a complex of pyridine and sulfur trioxide, and the aldehyde then extracted from the reaction mixture. Before further use, the solvent may be partially removed for concentration.

The reaction with a compound of formula III may be carried out at temperatures of −20 to 100° C. and preferably at 0 to 50° C. The reaction is expediently carried out in an organic solvent, preferably in halogenated hydrocarbons, for example methylene chloride, chloroform, 1,2-dichloroethane or tetrachloroethane. To bind the reaction water, it is advantageous to add a water-binding agent, for example anhydrous metal salts, such as sodium sulfate or calcium chloride, or silica gels. The hydroxylamine is added in at least equimolar quantities or in slight excess. The isolation may be carried out in a known manner, for example by evaporation of the solvent, filtration of the residue and crystallization or chromatographic separation of the filtrate. The compounds of formula IV are formed in high yields of up to 90% or more.

Process Step b)

Metal organic derivatives of a compound of formula V are for example those of formula X,

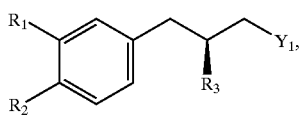

wherein $Y_1$ is an alkali metal (lithium, sodium and potassium) or —MeY, wherein Y is Cl, Br or iodine and Me is Mg, Zn, Hg or Cd. Preferred compounds are those wherein $Y_1$ is MgY. The preparation of metal organic derivatives from compounds of formula V is known and described in more detail in the example. The reaction is preferably carried out in ethers or aromatic hydrocarbons as solvents. Some examples are diethylether, dipropylether, dibutylether, methylpropylether, methylbutylether, tetrahydrofuran and dioxane, as well as benzene, toluene and xylene. The reaction temperature may be −70 to 100 and preferably −30 to 50° C. The compounds of formula IV and the metal organic derivatives of compounds of formula V can be used in equimolar quantities, or an excess of the compounds of said metal organic derivatives are used. One may proceed in such a way that first the said metal organic derivatives are prepared and these added without isolation to a solution of a compound of formula IV. The ratio of 5(S):5(R)-diastereomer is about 30:70. This ratio may be reversed and essentially increased for example to 70:30 or higher if the reaction is carried out in the presence of heavy metal salts, or if the said metal organic derivatives are transmetallated with heavy metal salts (see D. A. Sandham et al. in Tetrahedron Letters, Volume 41, Issue 51, pages 10090ff (2000)). Suitable metal salts are those from the group of lanthanides and the first and eighth subgroup of the periodic system of elements, for example Cu, Fe, Ni and preferably Ce. Especially suitable are the chlorides or sulfates of these metals. The compounds of formula VI may be isolated in the customary manner by extraction and removal of the solvent. Purification may be performed by distillation or chromatography. The pure 5(S)-diastereomer may be obtained by salt formation with chiral acids; or acylation with chiral acid derivatives and recrystallization or chromatography; or directly by chromatography on chiral columns. The yield may be as high as 80% or more.

Process Step c)

The removal of the hydroxyl group is expediently carried out by means of reduction, preferably in an aqueous-acidic medium. As reduction agent, hydrogen is preferred. This may be advantageously generated as nascent hydrogen by the addition of metals such as zinc or iron to the aqueous-acidic medium. Suitable acids are organic or inorganic acids, such as acetic acid, hydrochloric acid or sulfuric acid. The presence of heavy metal salts such as copper diacetate may be advantageous. The reaction temperature may be 0 to 80° C.

Process Step d)

The removal of the pseudoephedrine protecting group may be carried out in aqueous-acidic medium. Suitable acids are organic or inorganic acids, such as acetic acid, hydrochloric acid or sulfuric acid. The reaction temperature may be 0 to 80° C. In the context of the invention, process step d) may be carried out before process step c). It has proved advantageous to carry out process steps c) and d) at the same time in one reaction vessel. To this end, a copper salt and zinc powder may for example be placed in an aqueous acid such as acetic acid, followed by the addition of a solution of a compound of formula VI in aqueous acid. In this way, a compound of formula VII is obtainable directly from a compound of formula VI. The compound of formula VIII may be isolated by extraction. Purification may then be carried out by distillation or chromatography. The compound of formula VIII is obtained with a yield of more than 40% using the non-optimized process.

Process Step e)

The reaction of compounds of formula VIII with a compound $R_5NH_2$ on opening of the lactone ring to form compounds of formula IX is expediently carried out in the presence of alcohols or amines which are capable of forming activated carbonic esters or carboxamides. Such compounds are well-known. They may be 2-hydroxypyridine, N-hydroxycarboxamides and imides, and carboximides (N-hydroxysuccinimide). The solvents used are organic solvents, tertiary amines being of advantage, for example trimethylamine or triethylamine. The reaction temperature may range for example from approximately 40° C. to 150° C. and preferably from 50° C. to 120° C.

Process Step f)

The removal of protecting group Z is expediently carried out catalytically by hydrogenation in the presence of homogeneous or heterogeneous precious metal catalysts or Raney-Nickel. Homogeneous precious metal catalysts (Wilkinson catalysts) are soluble metal complexes of, for example, platinum, palladium, iridium, rhodium and ruthenium, which are known and have been described in the literature. Heterogeneous precious metal catalysts may for example be selected from the metals platinum, palladium, iridium, rhodium and ruthenium on, if necessary, solid carrier materials such as carbon, metal oxides or salts (aluminium oxide), quartz or silica gels. Organic solvents such as alcohols (methanol, ethanol) may advantageously be used as solvents. The reaction temperature may range for example from approximately 0° C. to 200° C. and preferably from 10° C. to 100° C. Hydrogenation may be carried out at normal pressure or increased pressure up to 100 bar, for example, and preferably up to 50 bar. It is further expedient to carry out the reaction in the presence of an organic amine (such as ethanolamine) in up to equimolar quantities or in slight excess. The yields are high and may be as much as 90% or more.

The compounds of formula I may be converted to addition salts in a manner known per se by treatment with monobasic or polybasic, inorganic or organic acids. Hemifumarates are preferred.

Also an object of the invention are compounds of formula IV,

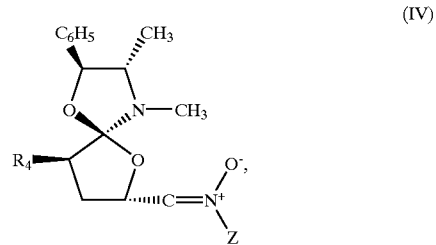

wherein $R_4$ and Z are as defined above, including the preferences.

A further object of the invention are compounds of formula XI in the form of 5(S)- or 5(R)-diastereomers or mixtures thereof,

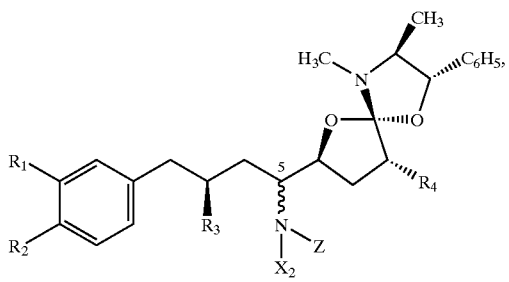

(XI)

wherein $R_1$, $R_2$, $R_3$, $R_4$ and Z are as defined above, including the preferences, and $X_2$ is H or OH.

A further object of the invention are compounds of formula XII in the form of 5(S)- or 5(R)-diastereomers or mixtures thereof,

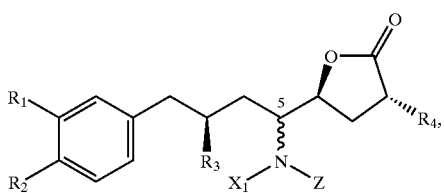

(XII)

wherein $R_1$, $R_2$, $R_3$, $R_4$ and Z are as defined above, including the preferences, and $X_2$ is H or OH.

A further object of the invention are compounds of formula XIII in the form of 5(S)- or 5(R)-diastereomers or mixtures thereof,

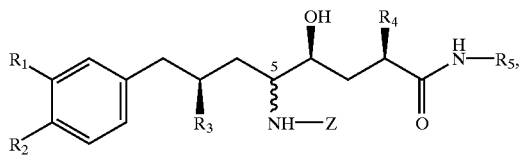

(IX)

wherein $R_1$, $R_2$, $R_3$, $R_4$, $R_5$ and Z are as defined above, including the preferences.

With the choice of compounds of formula IV, the compounds of formula 1, which per se are complex compounds, can be prepared in a convergent and simple manner, which is especially true of this enantioselective or diastereoselective synthesis. The total yield from all process steps may amount to 40% or more, which makes an industrial application feasible.

The following examples explain the invention in more detail.

A) Preparation of

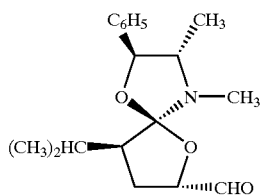

(A1) from

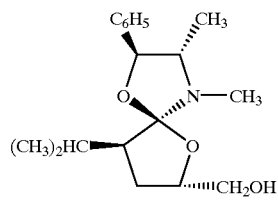

(1)

EXAMPLE A1

A solution of 0.31g (2 mmol) pyridine/sulfur trioxide complex and 2 mmol triethylamine in 3 ml dimethyl sulfoxide and methylene chloride (2:1) is added drop by drop over a period of 15 minutes to a solution of 0.2 g (0.65 mmol) compound 1 in 2 ml dimethyl sulfoxide and methylene chloride (2:1) cooled to 0° C. The reaction mixture is then heated to ambient temperature and stirred for one hour. The reaction mixture is then poured into 15 ml water while stirring. Extraction is carried out with 5×10 ml methylene chloride, the combined organic phases are washed with concentrated saline solution and then dried over sodium sulfate. After filtration, the volume is evaporated to 3 ml. This solution of A1 is used directly in the next reaction.

Example B1: Preparation of

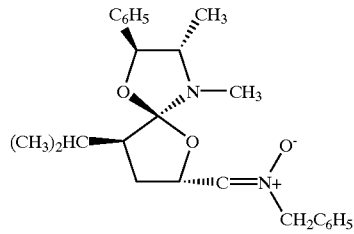

(B1)

To 3 ml of the solution described in example A1, 1.44 g anhydrous sodium sulfate is added at ambient temperature, followed by 0.089 g (0.72 mmol) benzylhydroxylamine. The mixture is then stirred for 2 hours at ambient temperature. Filtration is then carried out, followed by evaporation of the solvent and chromatography over silica gel with cyclohexane/acetone (3:2) containing one volume percent of triethylamine. Compound BI is obtained in a yield of 88% as a viscous yellow oil. After purification by flash chromatography [cyclohexane/acetone (3:2), 0.5 vol. % triethylamine) the compound crystallizes, and after recrystallization in cyclohexane B1 is obtained as white crystals with a melting point of 75° C.

Characterization: Melting point: 75–76° C.; $[\alpha]_D^{20}$=+27.4 (c=0.8, CHCl$_3$). $^1$H-NMR (300 MHz, CDCl$_3$): δ 7.47–7.30 (10H, m), 6.86 (1H, d, J=4.8 Hz), 5.24 (1H, m), 4.92 (2H, s), 4.49 (1H, d, J=8.6 Hz), 2.85 (1H, dq, J=6.4, 8.6 Hz), 2.35 (1H, ddd, J=9.6, 12.2, 12.4 Hz), 2.28 (3H, s), 2.17 (1H, ddd, 3.8, 8.4, 12.2 Hz), 1.86 (1H, dqq, J=3.8, 6.0, 6.2 Hz), 1.73 (1H, dt, J=8.4, 12.4 Hz), 1.13 (3H, d, J=6.0 Hz), 1.05 (3H, d, J=6.2 Hz), 0.92 (3H, d, J=6.4 Hz). $^{13}$C-NMR (75 MHz, CDCl$_3$): δ 141.91 (C=N), 140.20 (NCO$_2$), 132.40 (aromatic), 129.21 (2 C, aromatic), 128.81 (2 C, aromatic), 128.21 (2 C, aromatic), 127.74 (2 C, aromatic), 126.77 (2 C, aromatic), 122.17 (aromatic), 86.18 (OCH), 69.67 (OCH), 68.88 (NCH$_2$), 65.30 (NCH), 45.95 (NCH$_3$), 33.12 (CH$_2$), 30.84 (CH), 28.50 (CH), 22.12 (CH$_3$), 21.10 (CH$_3$), 15.43 (CH$_3$).

C) Preparation of

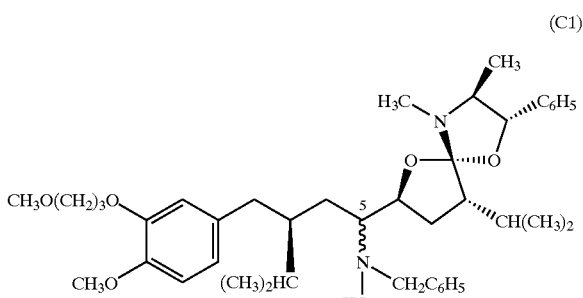

from B1 and

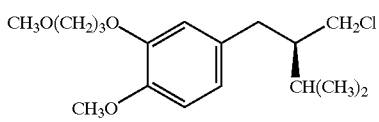

EXAMPLE C1

Half of a solution of 1.54 g (4.9 mmol) compound Z1 and 20 μl 1,2-dibromethane in 10 ml tetrahydrofuran is added drop by drop to a suspension of 0.18 g (7.3 mmol) magnesium powder in tetrahydrofuran containing a few crystals of iodine and heated to 75° C. After the yellow iodine color has faded, the other half is added dropwise over 15 minutes and then stirred for another 2 hours at 75° C. After cooling to ambient temperature, the reaction mixture is added drop by drop over 15 minutes to a solution of 0.96 g (2.4 mmol) compound D2 in 6 ml tetrahydrofuran which has been cooled to −10° C. The mixture is then stirred for 15 hours at −10° C. and 40 ml saturated aqueous ammonium chloride solution added. Extraction is carried out with 4×20 ml ethyl acetate, followed by drying over anhydrous sodium sulfate. The solvent is evaporated and the residue purified by flash chromatography (mobile phase cyclohexane/acetone 9:1, containing 0.5 vol. % triethylamine). Compound C1 is obtained in a yield of 77% as a colorless oil. The ratio of 5(S)- to 5(R)-stereoisomer is 30:70. The stereoisomers are separated by chromatography using Jobin Yvon Chromatospac at 6 atmospheres pressure (mobile phase cyclohexanelacetone 9:1, containing 0.5 vol. % triethylamine).

Characterization: Main diastereoisomer: $[\alpha]_D^{20}$=+54.1 (c=1.0 in CHCl$_3$)H-NMR (300 MHz, CDCl$_3$): δ 7.48–7.23 (10H, m), 6.77–6.75 (3H, m), 4.99 (1H, bs), 4.59 (1H, dt, J=4.1, 6.8 Hz), 4.50 (1H, d, J=8.8 Hz), 4.08 (1H, dt, J=6.4, 9.5 Hz), 4.00 (1H, dt, J=6.6, 9.5 Hz), 3.82 (3H, s), 3.80 (1H, d, J=13.7 Hz), 3.72 (1H, d, J=13.7 Hz), 3.54 (2H, t, J=6.2 Hz), 3.33 (3H, s), 2.94 (1H, dt, J=4.1, 8.0 Hz), 2.86 (1H, dq, J=6.1, 8.8 Hz), 2.70 (1H, dd, J=5.4, 13.7 Hz), 2.34 (1H, dd, J=9.0, 13.7 Hz), 2.26 (3H, s), 2.07 (2H, ddt, J=6.2, 6.4, 6.6 Hz), 2.05–1.43 (8H, m), 1.12 (3H, d, J=5.8 Hz), 1.08 (3H, d, J=5.1 Hz), 1.06 (3H, d, J=6.6 Hz), 0.96 (3H, d, J=6.1 Hz), 0.92 (3H, d, J=6.6 Hz). $^{13}$C-NMR (75 MHz, CDCl$_3$): δ 148.53 (arom), 147.72 (arom.), 141.20 (NCO$_2$), 139.32 (aromatic), 135.02 (aromatic), 129.36 (2 C, aromatic), 128.59 (2 C, aromatic), 128.43 (2 C, aromatic), 128.09 (aromatic), 127.41 (2 C, aromatic), 127.22 (aromatic), 121.93 (aromatic), 121.64 (aromatic), 114.54 (arom.), 111.91 (aromatic), 86.61 (OCH), 72.92 (OCH), 69.66 (OCH$_2$), 67.84 (OCH$_3$), 66.21 (OCH$_2$), 66.03 (OCH$_3$), 59.50 (NCH$_2$), 58.88 (NCH), 56.32 (NCH), 46.23 (CH), 42.90 (NCH$_3$), 36.20 (CH$_2$), 32.85 (CH$_2$), 31.72 (CH), 29.86 (CH$_2$), 29.47 (CH), 28.11 (CH), 26.39 (CH$_2$), 22.72 (CH$_3$), 21.62 (CH$_3$), 20.02 (CH$_3$), 17.75 (CH$_3$), 15.84 (CH$_3$). MALDI-TOF MS: 690.5 (M+H).

Secondary diastereoisomer: $^1$H-NMR (300 MHz, CDCl$_3$): δ 7.52–7.26 (10H, m), 6.86–6.72 (3H, m), 5.58 (1H, bs), 4.54 (1H, d, J=8.4 Hz), 4.48 (1H, m), 4.28 (1H, d, J=12.9 Hz), 4.09 (1H, t, J=6.3 Hz), 3.99 (1H, d, J=12.9 Hz), 3.86 (3H, s), 3.56 (2H, t, J=6.3 Hz), 3.36 (3H, s), 3.02–2.88 (2H, m), 2.66 (1H, dd, J=5.4, 13.7 Hz), 2.49 (1H, dd, J=9.0, 13.7 Hz), 2.34 (3H, s), 2.12–2.03 (2H, m), 1.92–1.51 (8H, m), 1.14 (3H, d, J=6.3 Hz), 1.06 (3H, d, J=5.6 Hz), 0.96 (3H, d, J=6.3 Hz), 0.91 (6H, d, J=7.0 Hz).

EXAMPLE C2

Preparation of Compound C1

Example C1 is repeated with 8 mmol cerium trichloride. The yield is similar to that in example C1. However, the ratio of 5(S)- to 5(R)-stereoisomer is 75:25.

D) Preparation of

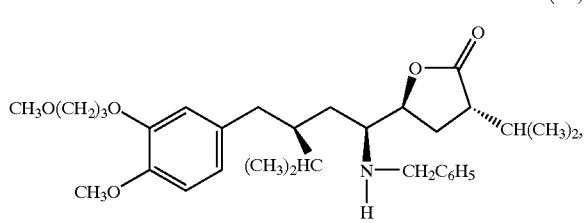

EXAMPLE D1

The removal of the pseudoephedrine group and the reductive removal of the hydroxyl group are carried out at the same time. To a solution of 0.0029 g (0.14mmol) copper (acetate)$_2$xH$_2$O in 0.4 ml acetic acid, 0.00474 g (0.725 mmol) zinc powder is added and the mixture stirred for 15 minutes at ambient temperature. A solution of 0.1 g (0.145 mmol) of the 5S-diastereomer of compound C1 in 0.8 ml acetic acid I water (3:1) is then added and stirred for 55 hours at ambient temperature. The mixture is filtered via Celite and then washed with a little water/ethyl acetate. The filtrate is extracted with 4×10 ml ethyl acetate and the combined organic phases then washed with water. The organic phase is separated off and dried with anhydrous sodium sulfate. After the solvent has been evaporated off, the residue is purified by flash chromatography (mobile phase cyclohexane/ethyl acetate 3:1). Compound D1 is obtained in a yield of 41% as a clear colorless liquid.

Characterization: $[\alpha]_D^{20}$=+6.3 (c=1.0, CHCl$_3$). $^1$H-NMR (300 MHz, CDCl$_3$): δ 7.36–7.20 (6H, m), 6.75 (1H, d, J=8.1 Hz), 6.68 (1H, d, J=1.9 Hz), 6.66 (1H, dd, J=1.9, 8.1 Hz), 4.35 (1H, ddd, J=4.1, 5.1, 8.5 Hz), 4.11 (1H, dt, J=6.6, 12.7 Hz), 4.05 (1H, dt, J=6.3, 12.7 Hz), 3.83 (3H, s), 3.69 (1H, d,J=13.2 Hz), 3.64 (1H, d, J=13.2 Hz), 3.58 (2H, t, J=6.1 Hz), 3.37 (3H, s), 2.82 (1H, ddd, J=4.1, 4.6, 8.5 Hz), 2.66 (1H, dd, J=4.9, 10.5 Hz), 2.63 (1H, dd, J=5.1, 10.5 Hz), 2.22–2.06 (5H, m), 1.93 (1H, ddd, J=6.8, 8.5, 13.4 Hz), 1.72 (1H, m), 1.51 (1H, m), 1.33 (1H, ddd, J=4.6, 7.6, 13.4 Hz), 1.28 (1H, bs), 1.15 (1H, ddd, J=4.4, 8.5, 13.4 Hz), 1.02 (3H, d, J=6.8 Hz), 0.94 (3H, d, J=6.8 Hz), 0.93 (3H, d, J=6.8 Hz), 0.86 (3H, d, J=6.8 Hz). $^{13}$C-NMR (75 MHz, CDCl$_3$): δ 179.35 (C=O), 148.58 (aromatic), 147.93 (aromatic), 140.68 (aromatic), 134.10 (aromatic), 128.63 (2 C, aromatic), 128.53 (2 C, aromatic), 127.28 (aromatic), 121.44 (aromatic), 114.63 (aromatic), 112.08 (aromatic), 82.02 (OCH), 69.62 (OCH$_2$), 66.36 (OCH$_2$), 58.91 (NCH), 57.65 (OCH$_3$), 56.26 (OCH$_3$), 53.43 (NCH$_2$), 46.20 (CH), 43.12 (CH), 36.68 (CH$_2$), 32.22 (CH$_2$), 29.89 (CH$_2$), 29.43 (CH), 29.39 (CH), 24.52 (CH$_2$), 20.68 (CH$_3$), 19.78 (CH$_3$), 18.60 (CH$_3$), 18.19 (CH$_3$).

E) Preparation of

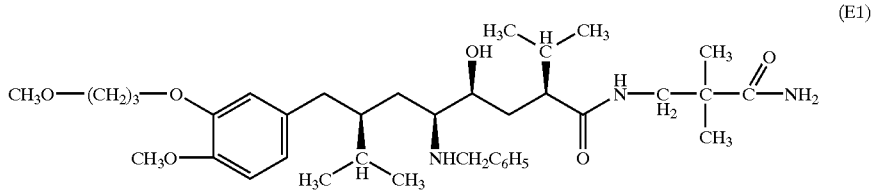

(E1)

EXAMPLE E1

A mixture of 0.591 g D1, 0.418 g 3-amino-2,2-dimethylpropionamide, and 0.023 g 2-hydroxypyridine in 5.9 ml triethylamine is stirred over a period of 16 hours at 90° C. Then 3.3 ml triethylamine is distilled off over a period of 0.5 hours, and the residue is agitated for a further 8.5 hours at 90° C. The cooled reaction mixture is extracted between ethyl acetate (3×500 ml), saturated aqueous sodium hydrogencarbonate solution (1×500 ml) and saturated sodium chloride solution (1×500 ml). The combined organic phases are dried over 4 g sodium sulfate, filtered and concentrated on a rotary evaporator. The residue is dried, and crude title compound E1 is obtained as an oil.

Characterization: $^1$H-NMR (300 MHz, CDCl$_3$): δ 7.37–7.20 (5H, m), 6.76 (1H, d, 8.1 Hz), 6.70 (1H, d, J=1.9 Hz), 6.67 (1H, dd, J=1.9, 8.1 Hz), 6.41 (1H, dd, J=6.0, 6.4 Hz), 6.35 (1H, bs), 5.52 (1H, bs), 4.10 (1H, dt, J=6.2,12.0 Hz), 4.06 (1H, dt, J=6.2, 12.0 Hz), 3.82 (3H, s), 3.64 (2H, s), 3.61 (1H, m), 3.58 (2H, t, J=6.2 Hz), 3.44 (1H, dd, J=6.4, 13.0 Hz), 3.39 (1H, dd, J=6.4, 13.0 Hz), 3.36 (3H, s), 2.59 (1H, dd, J=4.4, 13.0 Hz), 2.53 (1H, dt, J=4.0, 7.6 Hz), 2.18 (1H, dd, J=8.4, 13.0 Hz), 2.10 (2H, m), 1.92–1.23 (8H, m), 1.17 (2H, s), 0.96 (3H, d, J=6.8 Hz), 0.93 (3H, d, J=6.8 Hz), 0.91 (3H, d, J=6.8 Hz), 0.85 (3H, d, J=6.8 Hz).

F) Preparation of

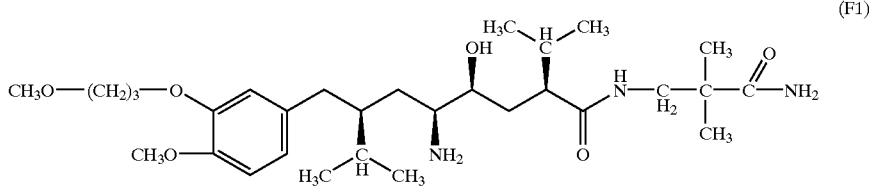

(F1)

EXAMPLE F1

A suspension of 0.12 g 10% Pd/C, 0.119 g (0.185 mmol) compound E1 and 0.185 mmol ethanolamine in 3 ml methanol is added to a pressurized vessel, 1 atmosphere of hydrogen pressure, is applied and the suspension then stirred for 3 hours at ambient temperature. Filtration is then carried out and the solvent evaporated off. Compound F1 is obtained in a yield of 87% as a colorless oil.

Characterization: $^1$H-NMR (300 MHz, CDCl$_3$): δ 6.82 (1H, d, J=8.1 Hz), 6.70 (1H, d, J=1.9 Hz), 6.68 (1H, dd, J=1.9, 8.1 Hz), 6.32 (1H, dd, J=6.0, 6.4 Hz), 5.40 (1H, bs), 4.97 (1H, d, J=9.0 Hz), 4.65 (1H, dd, J=4.8, 8.3 Hz), 4.12 (2H, t, J=6.2 Hz), 4.00 (1H, m), 3.86 (3H, s), 3.58 (2H, t, J=6.2 Hz), 3.56 (1H, dd, J=6.0, 13.8 Hz), 3.36 (3H, s), 3.23 (1H, dd, J=6.4, 13.8 Hz), 2.68 (1 h, dd, J=3.5, 13.6 Hz), 2.40 (2H, t, 6.2 Hz), 2.20–1.42 (9H, m), 2.05 (3H, s), 1.82 (3H, s), 1.23 (6H, s), 0.99 (3H, d, J=6.8 Hz), 0.91 (6H, d, J=6.8 Hz), 0.88 (3H, d, J=6.8 Hz). MALDI-TOF MS: 659.0 (M+Na), 674.9 (M+K).

What is claimed is:

1. A process for the preparation of compounds of formula I and their physiologically acceptable salts,

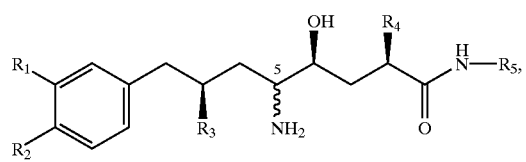

(I)

wherein

R$_1$ and R$_2$ are, independently of one another, H, C$_1$–C$_6$alkyl, C$_1$–C$_6$halogenalkyl, C$_1$–C$_6$alkoxy, C$_1$–C$_6$alkoxy-C$_1$–C$_6$alkyl, or C$_1$–C$_6$alkoxy-C$_1$–C$_6$alkyloxy, R$_3$ is C$_1$–C$_6$alkyl, R$_4$ is C$_1$–C$_6$alkyl, and R$_5$ is C$_1$–C$_6$alkyl, C$_1$–C$_6$hydroxyalkyl, C$_1$–C$_6$alkoxy-C$_1$–C$_6$-alkyl, C$_1$–C$_6$alkanoyloxy-C$_1$–C$_6$alkyl, C$_1$–C$_6$aminoalkyl, C$_1$–C$_6$alkylamino-C$_1$–C$_6$-alkyl, C$_1$–C$_6$-dialkylamino-C$_1$–C$_6$-alkyl, C$_1$–C$_6$-alkanoylamido-C$_1$–C$_6$-alkyl, HO(O)C—C$_1$–C$_6$-alkyl, C$_1$–C$_6$alkyl-O—(O)C—C$_1$–C$_6$alkyl, H$_2$N—C(O)—C$_1$–C$_6$alkyl, C$_1$–C$_6$alkyl-HN—C(O)—C$_1$–C$_6$alkyl or (C$_1$–C$_6$alkyl)$_2$N—C(O)—C$_1$–C$_6$-alkyl, comprising the steps a) reaction of a compound of formula II,

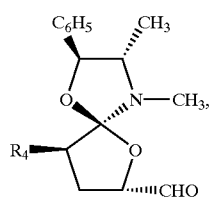

(II)

wherein $R_4$ is as defined above, with a hydroxylamine of formula ZNHOH (III), wherein Z is a removable protecting group, to form a compound of formula IV,

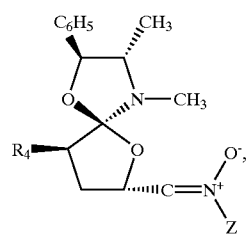

(IV)

b) reaction of a compound of formula IV with a metal organic derivative of a compound of formula V,

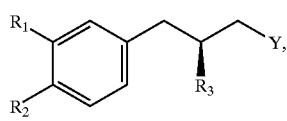

(V)

wherein $R_1$, $R_2$ and $R_3$ are as defined above and Y is Cl, Br or I, to form a compound of formula VI,

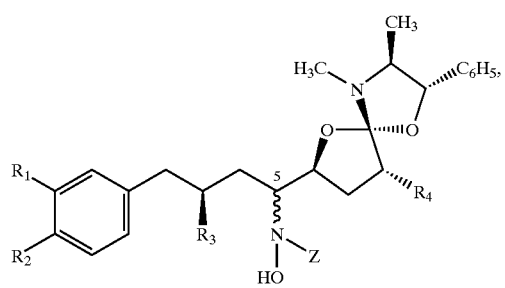

(VI)

c) removal of the hydroxyl group to form a compound of formula VII,

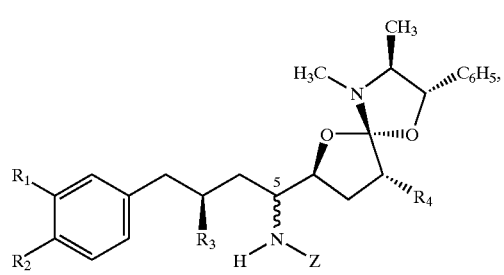

(VII)

d) removal of the pseudoephedrine protecting group to form compounds of formula VIII,

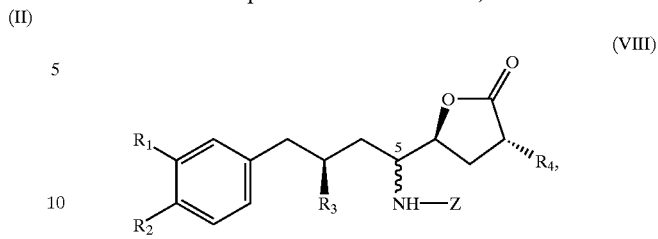

(VIII)

or performance of step d) before step c), or of steps c) and d) together in one reaction vessel, e) reaction of a compound of formula VIII with an amine of formula $R_5$—$NH_2$ to form a compound of formula IX

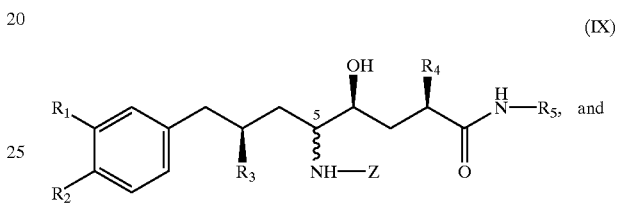

(IX)

and f) removal of protecting group Z for the preparation of compounds of formula I.

2. A process according to claim 1, comprising preparation of the 5(S)-diastereomer of formula Ia

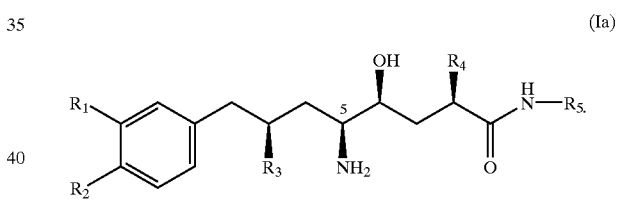

(Ia)

3. A process according to claim 1 wherein $R_1$ is $C_1$–$C_4$alkoxy or $C_1$–$C_4$alkoxy-$C_1$–$C_4$alkyloxy, $R_2$ is $C_1$–$C_4$alkoxy, $R_3$ is $C_1$–$C_4$alkyl, $R_4$ is $C_1$–$C_4$alkyl and $R_5$ is $H_2NC(O)$—$C_1$–$C_6$alkyl which optionally is N-monosubstituted or N-di-$C_1$–$C_4$alkyl-substituted.

4. A process according to claim 3 wherein $R_1$ is methoxy-$C_2$–$C_4$alkyloxy, $R_2$ is methoxy or ethoxy, $R_3$ is $C_2$–$C_4$alkyl, $R_4$ is $C_2$–$C_4$alkyl and $R_5$ is $H_2NC(O)$—$C_1$–$C_6$alkyl.

5. A process according to claim 4 wherein $R_1$ is 3-methoxy-prop-3-yloxy, $R_2$ is methoxy, $R_3$ and $R_4$ are 1-methyleth-1-yl, and $R_5$ is $H_2NC(O)$—$[C(CH_3)_2]$—$CH_2$—.

6. A process according to claim 1, wherein Z in formula III is benzyl.

7. A process according to claim 1, comprising the reaction of a compound of formula II immediately after preparation with a hydroxylamine.

8. A process according to claim 1, comprising a reaction temperature in process step a) of −20 to 50° C.

9. A process according to claim 1, wherein the metal organic derivatives in process step b) are those of formula X,

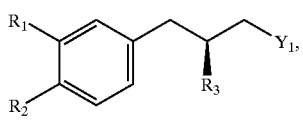

wherein $Y_1$ is an alkali metal or —MeY, wherein Y is Cl, Br or iodine and Me is Mg, Zn, Hg or Cd.

10. A process according to claim 1, comprising a reaction temperature in process step b) of −70 to 100° C.

11. A process according to claim 1, comprising the reaction in process step b) being carried out in the presence of a heavy metal salt.

12. A process according to claim 1, comprising the removal of the hydroxyl group in process step c) being carried out in an aqueous acidic medium with nascent hydrogen.

13. A process according to claim 1, comprising the removal of the pseudoephedrine group in process step d) being carried out in an aqueous acidic medium.

14. A process according to claim 1, comprising process steps c) and d) being carried out at the same time in one reaction vessel.

15. A process according to claim 1, comprising the reaction in process step e) being carried out in the presence of alcohols or amines, which form activated carbonic esters or carboxamides with the carboxylic acids of formula VIII.

16. A process according to claim 1, comprising a reaction temperature in process step e) of 40 to 150° C.

17. A process according to claim 1, comprising the removal of the protecting group Z in process step f) being carried out catalytically by hydrogenation in the presence of homogeneous or heterogeneous precious metal catalysts or Raney-Nickel.

18. A process according to claim 1, comprising a reaction temperature in process step f) of 0 to 200° C.

19. Compounds of formula IV,

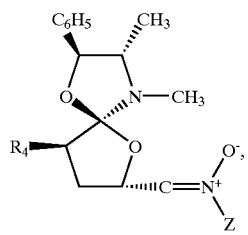

wherein $R_4$ and Z are as defined in claim 1.

20. Compounds of formula XI in the form of 5(S)— or 5(R)-diastereomers or mixtures thereof,

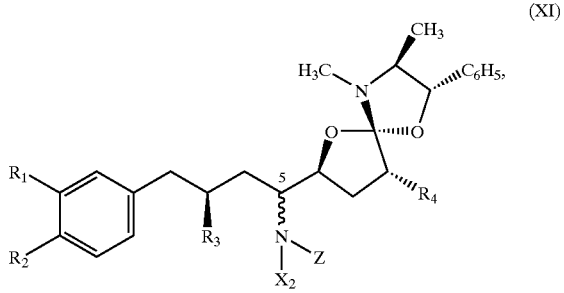

wherein $R_1$, $R_2$, $R_3$, $R_4$ and Z are as defined in claim 1 and $X_2$ is H or OH.

21. Compounds of formula XII in the form of 5(S)— or 5(R)-diastereomers or mixtures thereof,

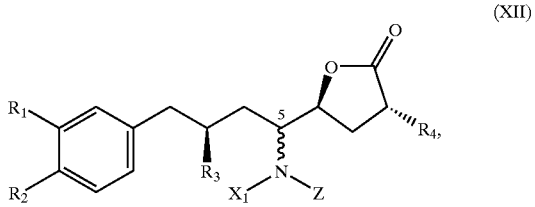

wherein $R_1$, $R_2$, $R_3$, and $R_4$ are as defined in claim 1, $X_2$ is H or OH, and Z is a silyl group or an unsubstituted or substituted mono-, di- or triarylmethyl group.

22. Compounds of formula IX in the form of 5(S)— or 5(R)-diastereomers or mixtures thereof,

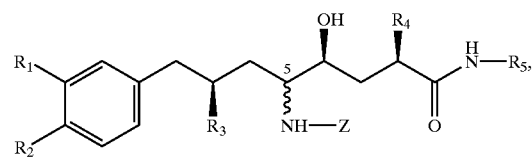

wherein $R_1$, $R_2$, $R_3$, $R_4$, and $R_5$ are as defined in claim 1, and Z is a silyl group or an unsubstituted or substituted mono-, di- or triarylmethyl group.

23. A process according to claim 11, wherein the heavy metal salt is a cerium salt.

* * * * *